US008733933B2

(12) United States Patent
Hirose et al.

(10) Patent No.: US 8,733,933 B2
(45) Date of Patent: May 27, 2014

(54) OPHTHALMOLOGIC APPARATUS AND BLOOD FLOW VELOCITY CALCULATION METHOD

(75) Inventors: Futoshi Hirose, Yokohama (JP); Hiroshi Imamura, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 34 days.

(21) Appl. No.: 13/306,185

(22) Filed: Nov. 29, 2011

(65) Prior Publication Data

US 2012/0140171 A1 Jun. 7, 2012

(30) Foreign Application Priority Data

Dec. 2, 2010 (JP) .................................. 2010-269740

(51) Int. Cl.
*A61B 3/14* (2006.01)
*A61B 3/12* (2006.01)
(52) U.S. Cl.
CPC ................. *A61B 3/1233* (2013.01); *A61B 3/12* (2013.01); *A61B 3/14* (2013.01)
USPC ....................................................... 351/206
(58) Field of Classification Search
USPC ......................................... 351/205, 206, 221
See application file for complete search history.

(56) References Cited

U.S. PATENT DOCUMENTS

| | | | |
|---|---|---|---|
| 4,213,678 A | | 7/1980 | Pomerantzeff |
| 5,549,114 A | * | 8/1996 | Petersen et al. ............... 600/504 |
| 7,530,692 B2 | * | 5/2009 | Yamaguchi et al. .......... 351/206 |
| 2006/0100528 A1 | | 5/2006 | Chan |
| 2007/0291230 A1 | | 12/2007 | Yamaguchi |
| 2008/0045848 A1 | | 2/2008 | Lacombe |

FOREIGN PATENT DOCUMENTS

| | | |
|---|---|---|
| CN | 1957266 A | 5/2007 |
| JP | 2003-180641 A | 7/2003 |
| JP | 2007-530197 A | 11/2007 |
| WO | 2006/105903 A2 | 10/2006 |

OTHER PUBLICATIONS

Martin et al.,Direct and Noninvasive Assessment of Parafoveal Capillary Leukocyte Velocity, American Academy of Ophthalmology, Dec. 2005, vol. 112, No. 12, pp. 2219-2224.
Hossain et al., "In Vivo Cell Tracking by Scanning Laser Ophthalmoscopy: Quantification of Leukocyte Kinetics", Investigative Ophthalmology & Visual Science, Sep. 1998, Vo. 39, No. 10, pp. 1879-1887, Chapter "SLO and Image Analysis".
Sakata et al., "Relationship between Macular Microcirculation and Progression of Diabetic Macular Edema",; Ophthalmology, J.B. Lippincott Co., Philadelphia, PA, US, vol. 113, No. 8, Aug. 1, 2006, pp. 1385-1391.

* cited by examiner

*Primary Examiner* — Mahidere Sahle
(74) *Attorney, Agent, or Firm* — Canon U.S.A., Inc., IP Division

(57) ABSTRACT

An ophthalmologic apparatus includes an irradiation unit irradiating a subject's eye with a measuring beam emitted by a scanning unit that performs scanning, a first acquisition unit acquiring a first image of the subject's eye based on the returned measuring beam from the subject's eye when the scanning unit performs scanning in a first sub scanning direction, a second acquisition unit acquiring a second image of the subject's eye based on the returned measuring beam travelling from the subject's eye, at timing different from that for the first image, while the scanning unit performs scanning in a second sub scanning direction opposite to the first sub scanning direction, and a calculation unit calculating blood flow velocity of the subject's eye based on a blood cell position in the first image, a blood cell position in the second image, and the sub scanning direction of the scanning unit.

14 Claims, 14 Drawing Sheets

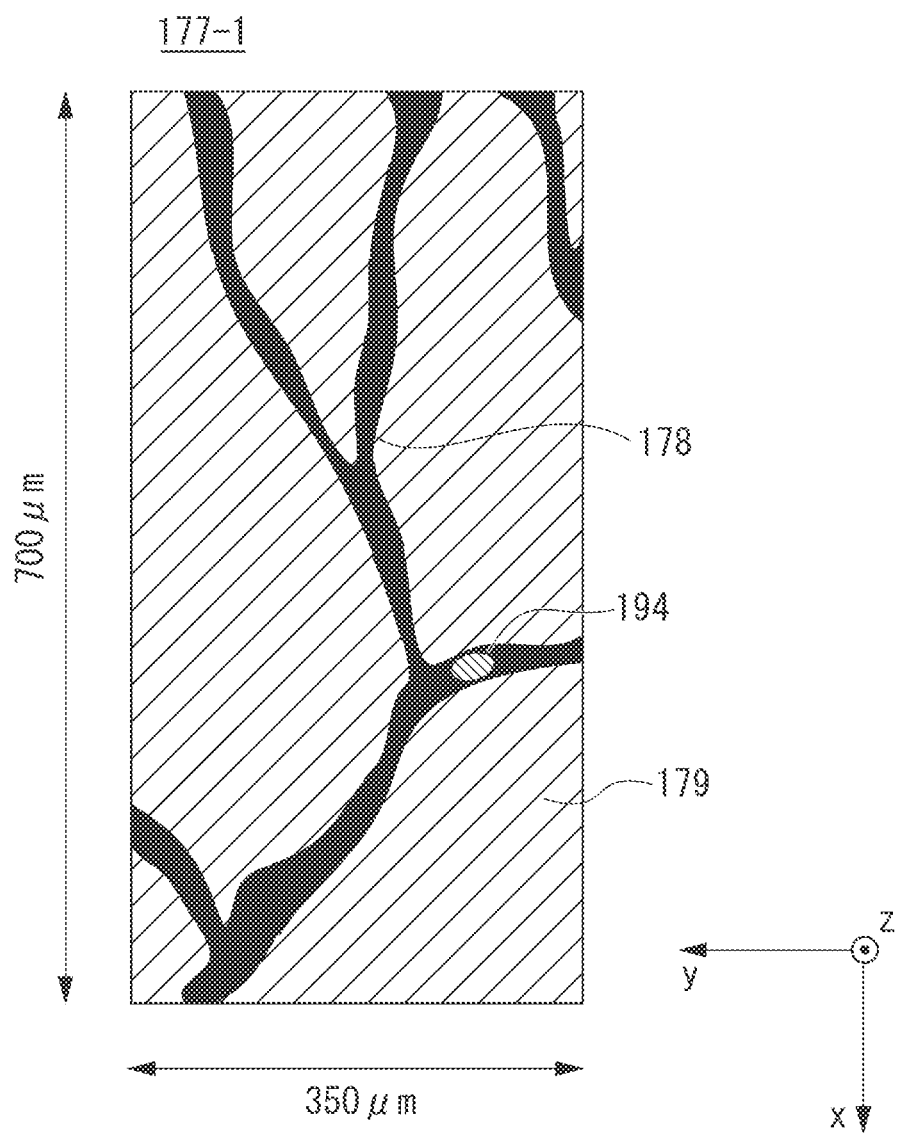

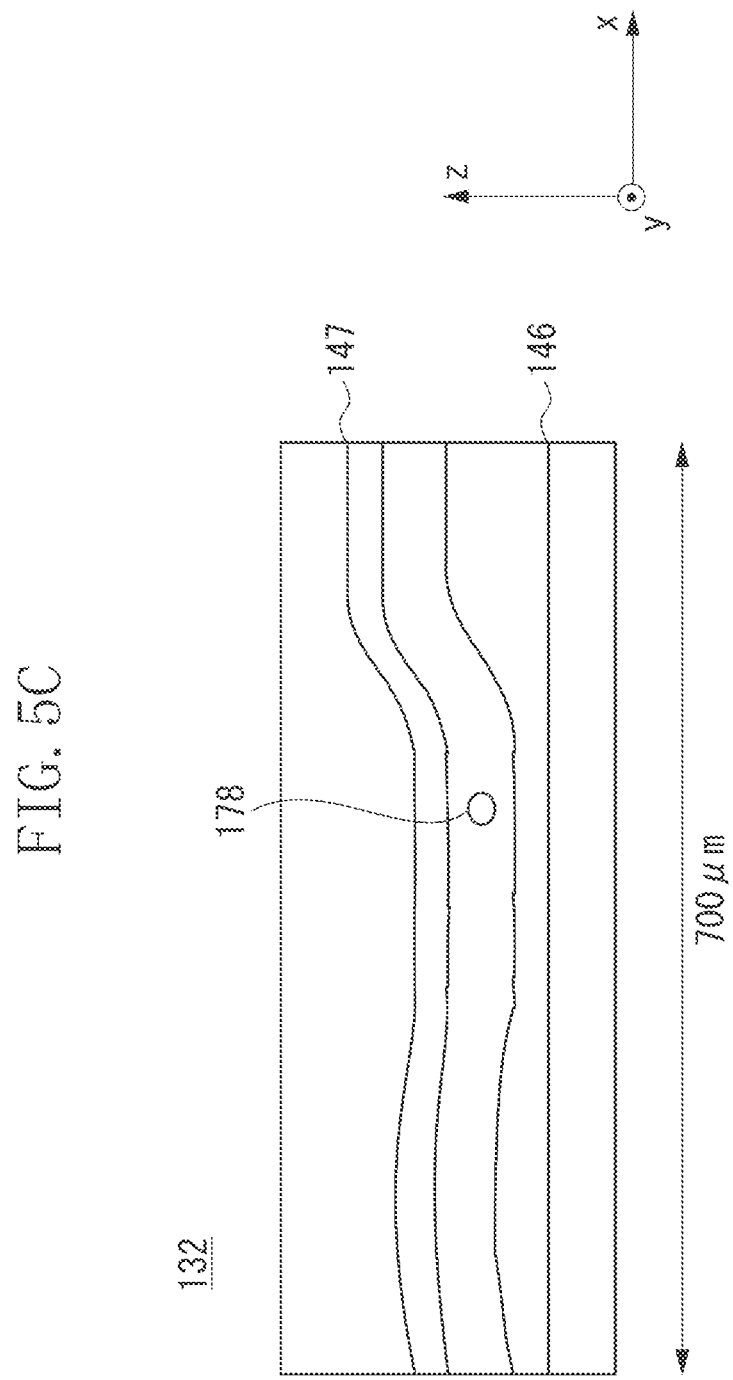

OPHTHALMOLOGIC APPARATUS AND BLOOD FLOW VELOCITY CALCULATION METHOD

BACKGROUND OF THE INVENTION

1. Field of the Invention

The present invention relates to a blood flow velocity calculation apparatus and a method. More specifically, the present invention relates to a blood flow velocity calculation apparatus and a method that can be used for ophthalmologic medical diagnosis.

2. Description of the Related Art

A scanning laser ophthalmoscope (SLO), which is an ophthalmologic apparatus operable based on the principle of confocal laser microscope, is an apparatus that can perform raster scanning on a fundus of an eye (hereinafter referred to a fundus) with a laser beam (i.e., a measuring beam) and can speedily obtain a high-resolution planar image of the fundus based on the intensity of a returned laser beam. Hereinafter, an apparatus capable of capturing a planar image is referred to as an SLO apparatus.

If a measuring beam having an increased beam diameter can be used in the SLO apparatus, the SLO apparatus can acquire a planar image of a retina that is excellent in horizontal resolution. However, when the beam diameter of the measuring beam becomes larger, the acquired planar image of a retina tends to deteriorate in S/N ratio and resolution due to an aberration that may be generated by a subject's eye.

An adaptive optics SLO apparatus is conventionally available to solve the above-described problem. The adaptive optics SLO apparatus includes a wavefront sensor that can perform real-time measurement of the aberration of the subject's eye. The adaptive optics SLO apparatus includes an adaptive optics system equipped with a wavefront correction device that can correct the aberration of the measuring beam or its returned beam that may be generated by the subject's eye. Thus, the adaptive optics SLO apparatus can acquire a planar image having excellent horizontal resolution.

Further, the adaptive optics SLO apparatus is conventionally usable to continuously acquire retinal planar images having excellent horizontal resolution and calculate the blood flow velocity based on a traveled distance of a blood cell in a capillary vessel, as discussed in "Joy A. Martin, Austin Roorda, Direct and Noninvasive Assessment of Parafoveal Capillary Leukocyte Velocity. Ophthalmology, 2005; 112: 2219." The calculation of the blood flow velocity discussed in this literature is performed based on time duration between acquisition of a preceding planar image and acquisition of a succeeding planar image (i.e., a time required to acquire a single planar image).

As described above, the SLO apparatus is an apparatus that includes a scanning unit configured to perform raster scanning on a retina with a measuring beam to acquire each retinal planar image. Therefore, the timing of an image capturing operation is variable depending on the position in an acquired planar image. Therefore, the measuring range for the blood flow velocity to be calculated may depend on the scanning direction of the scanning unit.

SUMMARY OF THE INVENTION

According to an aspect of the present invention, an ophthalmologic apparatus includes an irradiation unit configured to irradiate a subject's eye with a measuring beam emitted by a scanning unit that performs scanning, a first acquisition unit configured to acquire a first image of the subject's eye based on the returned measuring beam from the subject's eye when the scanning unit performs scanning in a first sub scanning direction, a second acquisition unit configured to acquire a second image of the subject's eye based on the returned measuring beam that travels from the subject's eye, at timing different from that for the first image, while the scanning unit performs scanning in a second sub scanning direction, which is opposite to the first sub scanning direction, and a calculation unit configured to calculate blood flow velocity of the subject's eye based on a blood cell position in the first image and a blood cell position in the second image as well as based on the sub scanning direction of the scanning unit.

The ophthalmologic apparatus according to the present invention can prevent the measuring range for the blood flow velocity from being varying depending on the scanning direction of the scanning unit.

Further features and aspects of the present invention will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

FIGS. 2A to 2G illustrate an example image acquisition method that can be realized by the SLO apparatus according to the first exemplary embodiment of the present invention.

FIGS. 5A, 5B, and 5C illustrate an example image acquisition method that can be realized by the composite apparatus according to the second exemplary embodiment of the present invention.

DESCRIPTION OF THE EMBODIMENTS

Figure 1:
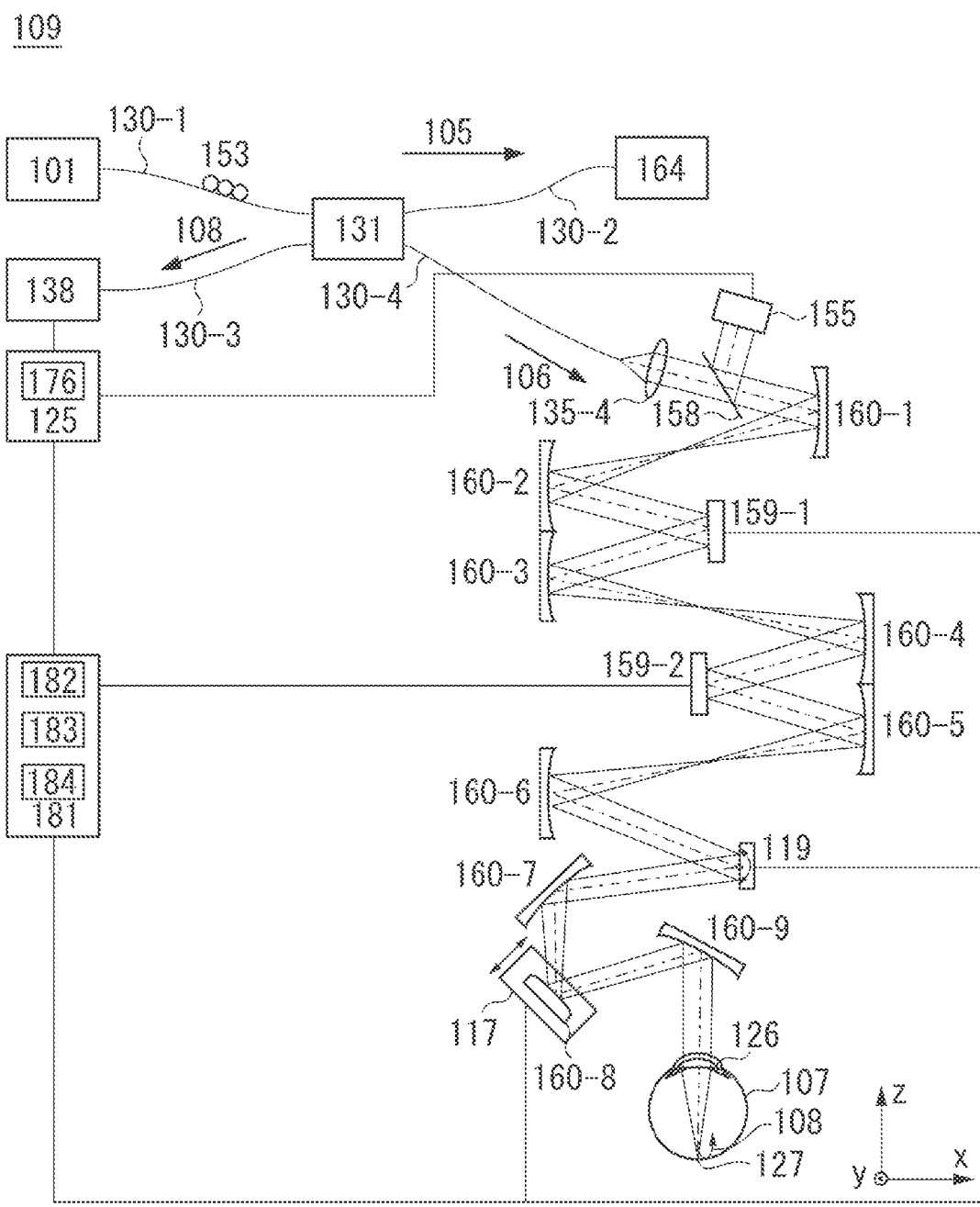
FIG. 1 illustrates an overall configuration of an SLO apparatus according to a first exemplary embodiment of the present invention.

Various exemplary embodiments, features, and aspects of the invention will be described in detail below with reference to the drawings.

A blood flow velocity calculation apparatus (i.e., an ophthalmologic apparatus) according to the present invention includes an irradiation unit configured to irradiate a subject's eye with a measuring beam that is scanned by a scanning unit (e.g., an XY scanner 119). Further, the apparatus includes a first acquisition unit (e.g., a personal computer 125) configured to acquire a first image (a planar image) of the subject's eye based on the returned measuring beam that travels from the subject's eye while the scanning unit performs scanning in a first sub scanning direction.

Further, the apparatus includes a second acquisition unit (e.g., the personal computer 125) configured to acquire a second image (a planar image) of the subject's eye based on the returned measuring beam that travels from the subject's eye, at timing different from that for the first image, while the scanning unit performs scanning in a second sub scanning direction, which is opposite to the first sub scanning direction.

Further, the apparatus includes a calculation unit (e.g., the personal computer 125) configured to calculate blood flow velocity of the subject's eye based on a blood cell position in the first image and a blood cell position in the second image as well as based on the sub scanning direction of the scanning unit.

Further, when the apparatus performs a scanning operation, the scanning speed in the first sub scanning direction can be set to be similar to the scanning speed in the second sub scanning direction. Further, the apparatus can drive the scanning unit in such a way as to change the scanning angle temporally in a triangular wave shape.

Further, the calculation unit of the apparatus can be configured to calculate the blood flow velocity of the subject's eye based on the blood cell position in the first image, the blood cell position in the second image, the sub scanning direction of the scanning unit, and the scanning speed of the scanning unit.

Further, the apparatus can include a display unit (e.g., a display device of the personal computer 125) configured to display the first image and the second image. Further, the apparatus can include an image processing unit (e.g., the personal computer 125) configured to perform image processing on the first image and the second image in such a way as to display a highlighted blood cell included in each of the first image and the second image displayed on the display unit.

Further, the apparatus can include a selection unit (e.g., a mouse of the personal computer 125) used to select the blood cell included in each of the first image and the second image displayed on the display unit.

Further, the calculation unit of the apparatus can be configured to calculate the blood flow velocity of the subject's eye based on the blood cell included in each of the first image and the second image selected by the selection unit. Further, the apparatus can include an image generation unit (e.g., the personal computer 125) configured to generate a spatiotemporal image based on the first image and the second image.

Further, the apparatus can include an aberration measurement unit (e.g., a wavefront sensor 155) configured to measure an aberration generated by the subject's eye. Further, the apparatus can include a spatial light modulation unit (e.g., a spatial optical modulator), which is positioned to be optically conjugate with the aberration measurement unit and configured to modulate at least one of the measuring beam and the optical feedback.

Further, the apparatus can include a control unit (e.g., a spatial optical modulator driver 184) configured to control a modulation amount by the spatial light modulation unit to correct the aberration based on a measurement result obtained by the aberration measurement unit.

Further, the apparatus can include a splitting unit (e.g., an optical coupler 131) configured to split light received from a light source into the measuring beam and a reference beam. Further, the apparatus can include a unit (e.g., the optical coupler 131) configured to cause the returned measuring beam traveling from the subject's eye to interfere with the reference beam traveling via a reference optical path.

Further, the apparatus can include a unit (e.g., a line sensor 139) configured to detect the intensity of an interference signal generated by the interference. The apparatus can include a tomographic image acquisition unit (e.g., the personal computer 125) configured to acquire a tomographic image of the subject's eye based on the intensity detected by the detection unit.

Further, the apparatus can include a conversion unit (e.g., the detector 138) configured to detect the returned measuring beam from the subject's eye and convert a detected beam into an electric signal. Further, the apparatus can include a light guiding unit (e.g., a movable beam splitter 161) positioned on an optical path connecting the light source and the subject's eye and guiding the returned beam to the conversion unit.

Further, the first acquisition unit and the second acquisition unit of the apparatus can be configured to acquire the first image of the subject's eye and the second image of the subject's eye based on the intensity of an electric signal that can be obtained by the conversion unit.

Further, the calculation unit of the apparatus can be configured to calculate blood flow velocity in a three-dimensional space, from the blood flow velocity, based on a three-dimensional stream of a blood vessel of the subject's eye acquired using the tomographic image.

Further, an example blood flow velocity calculation method according to the present invention includes an irradiating process of irradiating a subject's eye with a measuring beam emitted by a scanning unit that performs scanning, and a first acquisition process of acquiring a first image of the subject's eye based on the returned measuring beam from the subject's eye when the scanning unit performs scanning in the first sub scanning direction.

Further, the blood flow velocity calculation method includes a second acquisition process of acquiring a second image of the subject's eye based on the returned measuring beam that travels from the subject's eye, at timing different from that for the first image, while the scanning unit performs scanning in a second sub scanning direction, which is opposite to the first sub scanning direction. Further, the blood flow velocity calculation method includes a calculation process of calculating the blood flow velocity of the subject's eye based on the blood cell position in the first image and the blood cell position in the second image as well as based on the sub scanning direction of the scanning unit.

The apparatus includes an irradiation unit (which may be referred to as "illumination optical system") configured to irradiate the subject's eye with the measuring beam when the scanning unit performs scanning. Further, the apparatus includes an acquisition unit configured to acquire the first image (e.g., a first planar image) of the subject's eye based on the returned measuring beam that travels from the subject's eye while the scanning unit performs scanning in the first sub scanning direction and also acquire the second image (e.g., a second planar image) of the subject's eye based on the returned beam that travels from the subject's eye, at timing different from that for the first image, while the scanning unit performs scanning in the second sub scanning direction (e.g., a direction opposite to the first sub scanning direction).

Further, the apparatus includes a calculation unit configured to calculate the blood flow velocity of the subject's eye based on scanning information including information relating to the first and second sub scanning directions (e.g., scanning speed and scanning interval of the scanning unit). Thus, the apparatus can calculate the blood flow velocity considering the scanning direction of the scanning unit. As a result, the apparatus can calculate the blood flow velocity in a relatively wide measuring range.

In the present exemplary embodiment, it is desirable that the blood flow velocity calculation apparatus includes an indication unit configured to indicate a first position of the first image (e.g., a partial image including a blood cell) and a second position of the second image (e.g., a partial image including a blood cell). For example, the indication unit is a mouse that can be used to move a cursor. Further, the indication unit can be configured to indicate an image having intensity larger than a predetermined value.

Further, it is desirable that the apparatus is configured to calculate the blood flow velocity of the subject's eye based on the first and second positions as well as based on scanning speed and scanning interval of the scanning unit (namely, based on time duration between acquisition of the first position and acquisition of the second position as well as based on the distance traveled by the blood cell during the time duration).

Thus, the apparatus can use not only acquisition time of the first planar image but also scanning time (i.e., scanning speed and scanning interval of the scanning unit) of the scanning unit that scans the distance from the first position to the second position in the second image. Thus, the apparatus can calculate the blood flow velocity accurately using the time duration between acquisition of the blood cell position (i.e., first position) in the first planar image and acquisition of the blood cell position (i.e., second position) in the second planar image by the scanning unit.

Exemplary embodiments according to the present invention are described in detail below. An optical image capturing apparatus according to a first exemplary embodiment is an SLO apparatus that includes an adaptive optics system. The SLO apparatus can capture a planar image (i.e., an SLO image) of a target retina having excellent horizontal resolution, and can calculate the blood flow velocity based on the acquired planar image.

The SLO apparatus according to the present exemplary embodiment includes a spatial optical modulator that can correct optical aberration of a subject's eye to acquire a planar image. The SLO apparatus according to the present exemplary embodiment can obtain an excellent planar image that is not influenced by diopter or optical aberration of the subject's eye.

The SLO apparatus according to the present exemplary embodiment includes an adaptive optics system to capture a planar image having excellent horizontal resolution. However, the adaptive optics system may not be required if the SLO apparatus can capture an image of a blood vessel or a blood cell appropriately.

First, a schematic configuration of an SLO apparatus 109 according to the present exemplary embodiment is described in detail below with reference to FIG. 1.

An optical coupler 131 can split light received from a light source 101 into a reference beam 105 and a measuring beam 106. The SLO apparatus 109 can guide the measuring beam 106 to a subject's eye 107 (i.e., an observation target) via a single mode fiber 130-4, first and second spatial optical modulators 159-1 and 159-2, an XY scanner 119, and a plurality of spherical mirrors 160-1 to 160-9.

The measuring beam 106 reflects and scatters when it meets the subject's eye 107, and travels as an returned beam 108 toward a detector 138. The detector 138 can convert the light intensity of the returned beam 108 into a voltage signal. The detector 138 can form a planar image of the subject's eye 107 based on the obtained voltage signal. Further, the detector 138 can calculate blood flow velocity based on the acquired planar image.

The optical system according to the present exemplary embodiment is not limited to a reflection optical system that uses spherical mirrors, and can be configured as a refraction optical system including a plurality of lenses instead of using the spherical mirrors. Further, the optical system according to the present exemplary embodiment can be configured to include transmission type spatial optical modulators instead of using reflection type spatial optical modulators.

The light source 101 and its peripheral components have the following configuration. The light source 101 is a super luminescent diode (SLD), which is a representative low-coherent light source. The light source 101 can emit light having a wavelength of 830 nm and a bandwidth of 50 nm. The low-coherent light source according to the present exemplary embodiment is useful to acquire a planar image having a smaller speckle noise component. Further, the type of the light source is not limited to the SLD, and can be any other type, such as amplified spontaneous emission (ASE), if it can emit low-coherent light.

Further, when a target to be measured is an eye, it is desirable that the wavelength is in the near infrared ray range. Further, it is desirable that the wavelength is sufficiently short (830 nm in the present exemplary embodiment) because the wavelength influences the horizontal resolution of an obtained planar image. The wavelength to be selected for the light source 101 is variable depending on an observation target to be measured.

The light emitted from the light source 101 can be guided into the optical coupler 131 via a single mode fiber 130-1 and split into the reference beam 105 and the measuring beam 106 at a ratio of 96:4. The SLO apparatus 109 includes a polarizing controller 153.

The reference beam 105 travels along the following optical path. The reference beam 105 split by the optical coupler 131 can reach a quantity-of-light measurement apparatus 164 via an optical fiber 130-2. The quantity-of-light measurement apparatus 164 can measure the quantity of the reference beam 105 and monitor the quantity of the reference beam 105.

The measuring beam 106 travels along the following optical path. The measuring beam 106 split by the optical coupler 131 can reach a lens 135-4 via the single mode fiber 130-4. The measuring beam 106, after passing through the lens 135-4, travels as a parallel beam having a beam diameter of 4 mm. Then, the measuring beam 106 passes through a beam splitter 158 and, after being reflected by the spherical mirrors 160-1 and 160-2 sequentially, can reach the first spatial optical modulator 159-1.

In the present exemplary embodiment, the first spatial optical modulator 159-1 is disposed in a predetermined direction in which the first spatial optical modulator 159-1 can modulate the phase of the P polarization (parallel to the drawing surface).

Further, the measuring beam 106 can be modulated by the first spatial optical modulator 159-1 and reflected by the spherical mirrors 160-3 and 160-4 sequentially, and then can reach the second spatial optical modulator 159-2. In the present exemplary embodiment, the second spatial optical modulator 159-2 is disposed in a predetermined direction in which the second spatial optical modulator 159-2 can modulate the phase of the S polarization (perpendicular to the drawing surface).

In the present exemplary embodiment, each of the spatial optical modulators 159-1 and 159-2 performs modulation utilizing the orientation property of a liquid crystal. Therefore, each spatial optical modulator can modulate a polarizing component of a specific direction. Therefore, as described above, it is feasible to perform modulation for every polarizing component of the measuring beam 106 by continuously performing P polarizing component modulation and S polarizing component modulation on the measuring beam 106.

As described above, it is desirable that the orientation direction of the liquid crystal provided in the spatial optical modulator 159-1 is perpendicular to the orientation characteristics of the liquid crystal provided in the spatial optical modulator 159-2. In practice, the orientation directions of the spatial optical modulators 159-1 and 159-2 need not be perpendicular to each other but must be different from each other.

In the present exemplary embodiment, a personal computer 125 can control a spatial optical modulator driver 184 provided in a driver unit 181 to drive both of the spatial optical modulators 159-1 and 159-2.

Further, the measuring beam 106 can be modulated by the second spatial optical modulator 159-2 and reflected by the spherical mirrors 160-5 and 160-6 sequentially, and then can reach a mirror of the XY scanner 119. To simplify the explanation, the XY scanner 119 illustrated in FIG. 1 has only one mirror. However, in an actual arrangement, two mirrors are disposed adjacently for an X scanner and a Y scanner. The XY scanner 119 can perform raster scanning on a retina 127 in a direction perpendicular to the optical axis. Further, the center of the measuring beam 106 is adjusted to coincide with a rotational center of the mirror provided in the XY scanner 119.

In the present exemplary embodiment, the X scanner is a resonance scanner that can perform scanning with the measuring beam 106 in a direction parallel to the drawing surface. The driving frequency of the X scanner is approximately 7.9 kHz. Further, the Y scanner is a Galvano scanner that can perform scanning with the measuring beam 106 in a direction perpendicular to the drawing surface. The driving waveform of the Y scanner has a triangular shape. The frequency of the Y scanner is 38 Hz.

The driving frequency of the Y scanner is an important parameter to determine a frame rate of an image capturing operation to be performed by the SLO apparatus 109, in calculating the blood flow velocity. However, any other driving frequency is selectable depending on the blood flow velocity to be measured or depending on the measuring range.

In the present exemplary embodiment, the X scanner performs main scanning (horizontal scanning) and the Y scanner performs sub scanning (vertical scanning). More specifically, high-speed scanning is the main scanning and low-speed scanning is the sub scanning.

In the present exemplary embodiment, the personal computer 125 can control an optical scanner driver 182 provided in the driver unit 181 to drive the XY scanner 119. The spherical mirrors 160-7 to 160-9 constitute an optical system that can perform scanning on the retina 127. The optical system has a role to scan the retina 127 with the measuring beam 106 around a fulcrum positioned in the vicinity of a cornea 126.

In the present exemplary embodiment, the measuring beam 106 has a beam diameter of 4 mm. However, the beam diameter of the measuring beam 106 may be large enough to acquire a high-resolution tomographic image.

Further, the driver unit 181 can move an electric stage 117 in a direction indicated by an arrow to adjust the position of the associated spherical mirror 160-8. In the present exemplary embodiment, the personal computer 125 can control an electric stage driver 183 provided in the driver unit 181 to drive the electric stage 117.

When the driver unit 181 moves the electric stage 117 to adjust the position of the spherical mirror 160-8, the measuring beam 106 can be focused on a predetermined layer of the retina 127 of the subject's eye 107 and can be visually recognized. Further, for example, if the subject's eye 107 has refraction abnormality, it is useful to adjust the position of the spherical mirror 160-8.

The measuring beam 106 reflects and scatters on the retina 127 when the measuring beam 106 meets the subject's eye 107 and travels as the returned beam 108 toward the optical coupler 131 again, and reaches the detector 138 via a single mode fiber 130-3. The detector 138 is, for example, a high-speed and sensitive optical sensor, such as Avalanche Photo Diode (APD) or Photomultiplier Tube (PMT).

The second spatial optical modulator 159-2 and the first spatial optical modulator 159-1 can modulate the returned beam 108 for both of the S polarizing component and the P polarizing component. Further, apart of the returned beam 108 split by the beam splitter 158 reaches a wavefront sensor 155. The wavefront sensor 155 can measure an aberration of the returned beam 108 generated in the subject's eye 107.

In the present exemplary embodiment, the SLO apparatus 109 includes only one wavefront sensor 155. However, the SLO apparatus 109 can be configured to include two wavefront sensors to measure the aberration for each polarizing component. The wavefront sensor 155 is electrically connected to the personal computer 125. In the present exemplary embodiment, the spherical mirrors 160-1 to 160-9 are disposed in such a way that the cornea 126, the XY scanner 119, the wavefront sensor 155, and the spatial optical modulators 159-1 and 159-2 are optically conjugate with each other.

Therefore, the wavefront sensor 155 can measure the aberration of the subject's eye 107. Further, the spatial optical modulators 159-1 and 159-2 can correct the aberration of the subject's eye 107.

Further, when the personal computer 125 performs real-time control for the spatial optical modulators 159-1 and 159-2 based on the aberration (i.e., a measurement result of the wavefront sensor 155), the aberration generated by the subject's eye 107 can be corrected, and a planar image having excellent horizontal resolution can be acquired.

In the present exemplary embodiment, the spherical mirror 160-8 can be replaced by a cylindrical mirror depending on the aberration (refraction abnormality) of the subject's eye 107.

Further, a new lens can be additionally placed on the optical path of the measuring beam 106. In the present exemplary embodiment, the SLO apparatus 109 uses the measuring beam 106 to realize the aberration measurement by the wavefront sensor 155. However, any other light source is usable for the aberration measurement. Further, any other optical path dedicated to the aberration measurement can be provided.

For example, a beam splitter is usable to cause aberration measuring light to enter at a point positioned between the spherical mirror 160-9 and the cornea 126.

A measurement system according to the present exemplary embodiment has the following configuration. The SLO apparatus 109 can acquire a planar image (SLO image) that can be constituted based on the returned beam 108 from the retina 127.

The returned beam 108, i.e., the light having reflected and scattered on the retina 127, reaches the detector 138 via the spherical mirrors 160-1 to 160-9, the spatial optical modulators 159-1 and 159-2, and the optical coupler 131. The detector 138 converts the light intensity into a voltage signal.

An analog/digital (AD) board 176 provided in the personal computer 125 converts the voltage signal obtained by the detector 138 into a digital value. The personal computer 125 performs data processing in synchronization with an operation of the XY scanner 119 or the driving frequency thereof to form a planar image. In the present exemplary embodiment, the data fetch rate of the AD board 176 is 15 MHz.

Further, a part of the returned beam 108 split by the beam splitter 158 reaches the wavefront sensor 155. The wavefront sensor 155 measures the aberration of the returned beam 108. The wavefront sensor 155 is a Shack-Hartmann wavefront sensor. Thus, the wavefront sensor 155 can express the obtained aberration (i.e., the aberration of the subject's eye 107) using Zernike polynomials.

The Zernike polynomial expression includes a tilt term, a defocus term, an astigmatism term, a coma term, and a trifoil term.

Next, an example planar image (SLO image) acquisition method is described below with reference to FIGS. 2A to 2G. The SLO apparatus 109 can continuously acquire planar images (i.e., images on a plane perpendicular to the optical axis) of the retina 127 by controlling the XY scanner 119 while causing the detector 138 to acquire the intensity of the returned beam 108.

In the present exemplary embodiment, the SLO apparatus 109 continuously captures first planar images when the XY scanner 119 moves toward the positive Y axis and continuously captures second planar images when the XY scanner 119 moves toward the negative Y axis.

Figure 2A:
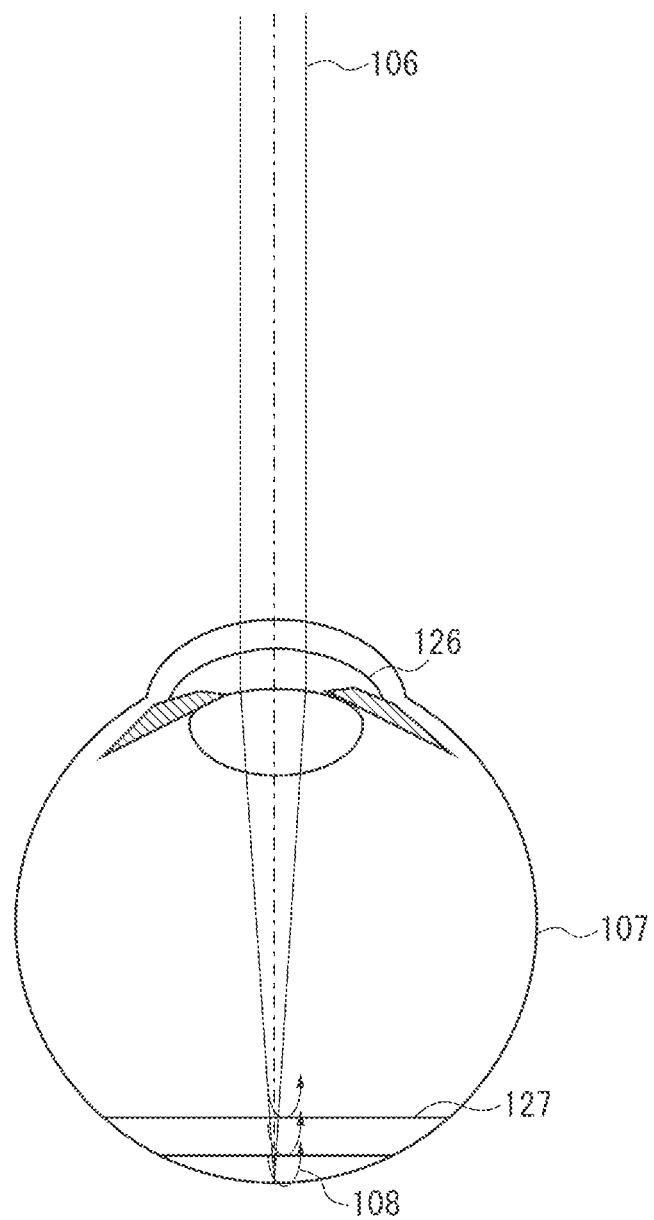

FIG. 2A schematically illustrates the subject's eye 107, which can be observed by the SLO apparatus 109. As illustrated in FIG. 2A, the measuring beam 106 reaches the retina 127 after passing through the cornea 126, and reflects and scatters at various positions, and then travels as the returned beam 108 to reach the detector 138.

Figure 2B:
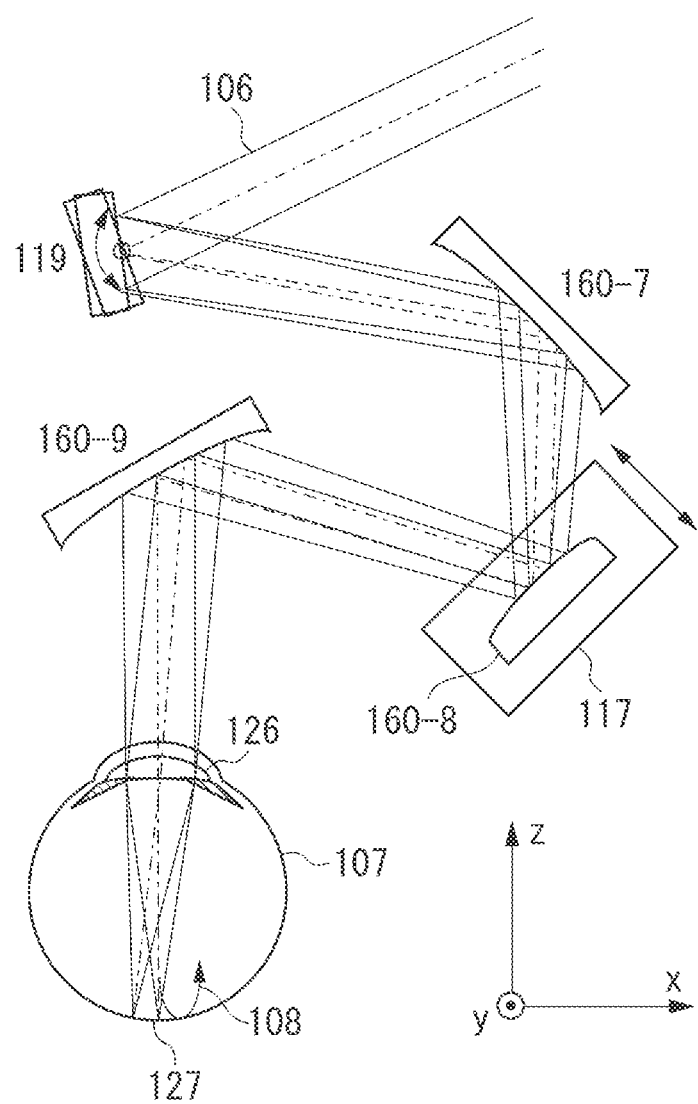

Further, as illustrated in FIG. 2B, information at each position along the X axis can be obtained by detecting the intensity of the returned beam 108 while driving the XY scanner 119 along the X axis.

Figure 2C:
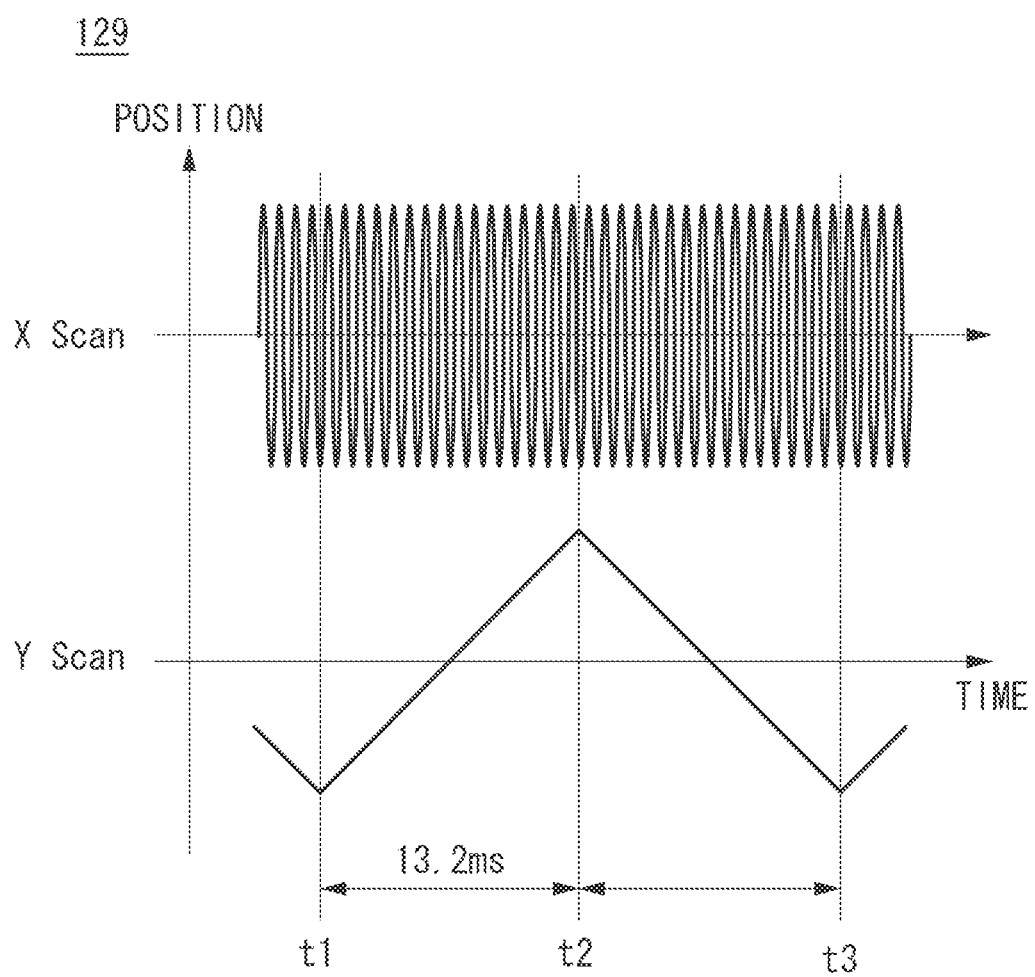

FIG. 2C is a timing chart 129 illustrating an example operation of the XY scanner 119. In FIG. 2C, the abscissa axis represents time and the ordinate axis represents measuring beam position in an image capturing range 192 of the retina 127.

Figure 2D:
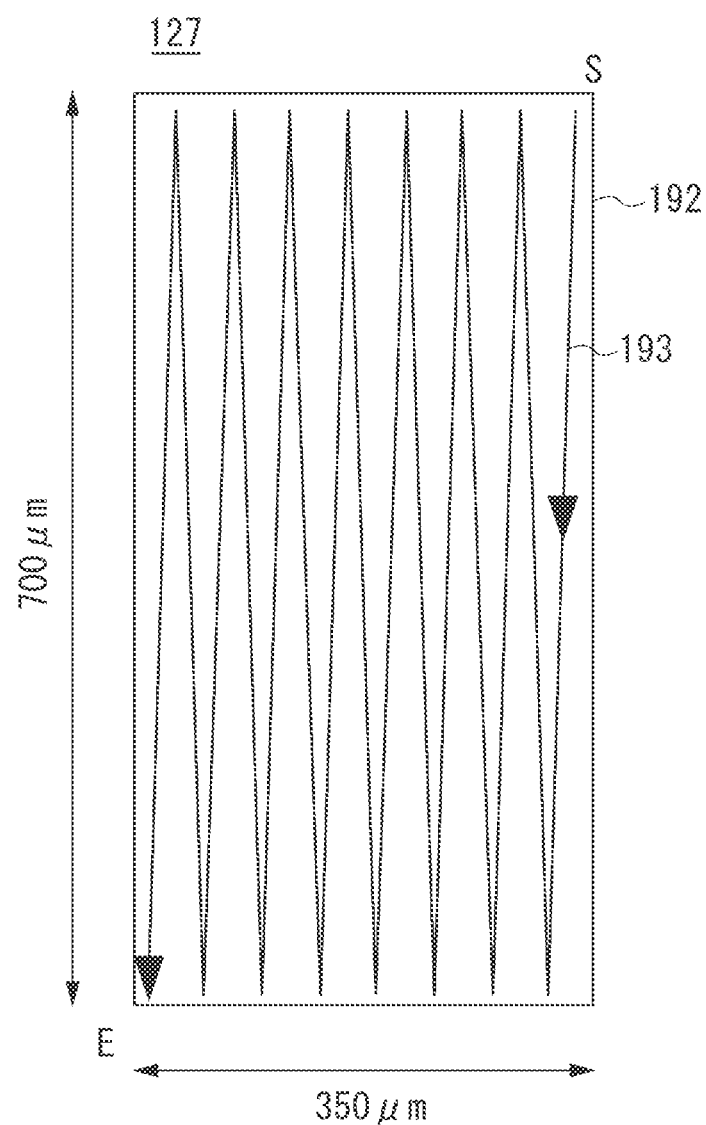

Further, the personal computer 125 controls the driver unit 181 to simultaneously drive the X axis and the Y axis of the XY scanner 119 in a time duration between time t1 and time t2 of the timing chart 129 illustrated in FIG. 2C. In this case, as illustrated in FIG. 2D, the XY scanner 119 performs raster scanning with the measuring beam 106 along a locus 193 in the image capturing range 192 where the retina 127 is present. When the detector 138 detects the intensity of the returned beam 108, the personal computer 125 can obtain a two-dimensional intensity distribution of the returned beam 108, i.e., a planar image. The planar image obtained in this case is referred to as a first planar image 177-1 (see FIG. 2E).

The first planar image 177-1 includes a brighter region that corresponds to a photoreceptor cell group 179 where the intensity of the returned beam 108 is relatively large, and a darker region that corresponds to a blood vessel 178 where the intensity of the returned beam 108 is relatively low. The first planar image 177-1 includes a brighter region that corresponds to a blood cell 194 included in the blood vessel 178. In the present exemplary embodiment, the planar image 177 has a size of 700 μm×350 μm.

Further, in FIG. 2D, point S and point E of the locus 193 correspond to time t1 and time t2 illustrated in FIG. 2C, respectively. The time period between time t1 and time t2 is approximately 13.2 ms. More specifically, the time required to capture the first planar image 177-1 is 13.2 ms. The above-described time is based on the driving frequency 38 Hz of the Y scanner.

Figure 2F:
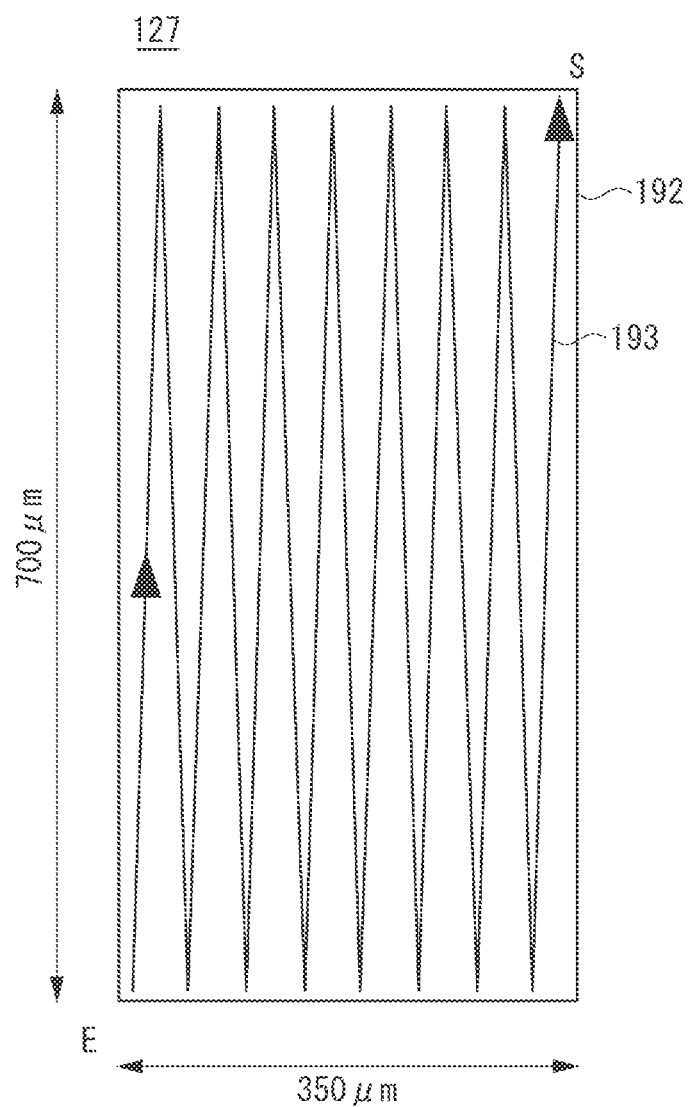
Figure 2G:
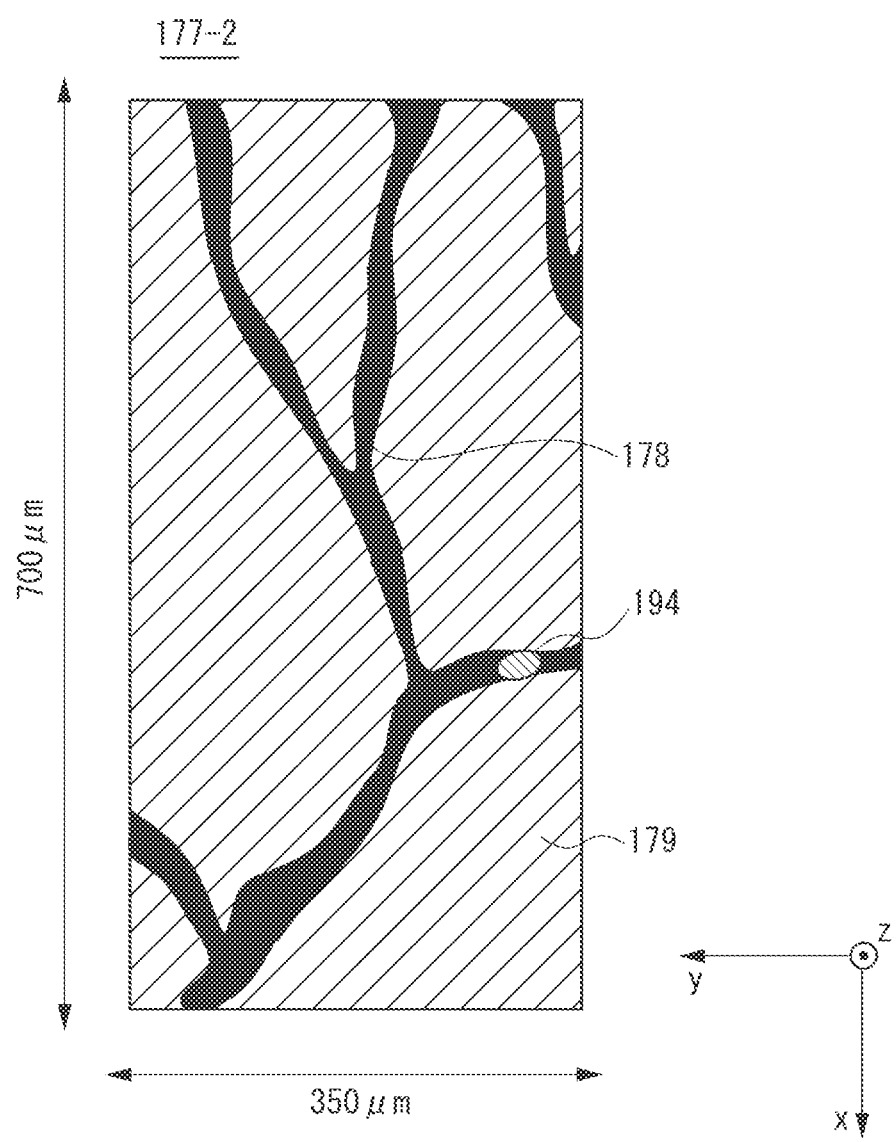

Similarly, the personal computer 125 controls the driver unit 181 to simultaneously drive the X axis and the Y axis of the XY scanner 119 in a time duration between time t2 and time t3 of the timing chart 129 illustrated in FIG. 2C. In this case, as illustrated in FIG. 2F, the XY scanner 119 performs raster scanning with the measuring beam 106 along the locus 193 in the image capturing range 192 where the retina 127 is present. When the detector 138 detects the intensity of the returned beam 108, the personal computer 125 can obtain a second planar image 177-2 (see FIG. 2G). The second planar image 177-2 includes a brighter region that corresponds to the photoreceptor cell group 179, a darker region that corresponds to the blood vessel 178, and a brighter region that corresponds to the blood cell 194.

It is understood that the blood cell 194 has traveled a distance in the blood vessel 178 between the capturing timing of the first planar image 177-1 and the capturing timing of the second planar image 177-2, which are captured continuously. Further, to simplify the description, FIGS. 2D and 2F schematically illustrate the locus 193 based on a smaller number of scanning operations performed in the X direction.

Further, the personal computer 125 can extract the blood vessel 178 including the blood cell 194 from a plurality of continuously acquired planar images 177. The personal computer 125 can generate a spatiotemporal image by overlapping the extracted blood vessel images in the captured order. Thus, the personal computer 125 can easily detect the moving blood cell 194 or the blood flow velocity.

Next, an example method for calculating the blood flow velocity based on continuously acquired planar images is described with reference to FIGS. 3A and 3B. The SLO apparatus 109 can continuously acquire planar images while the XY scanner 119 continuously performs raster scanning in image capturing range where the retina 127 is present.

Figure 3A:
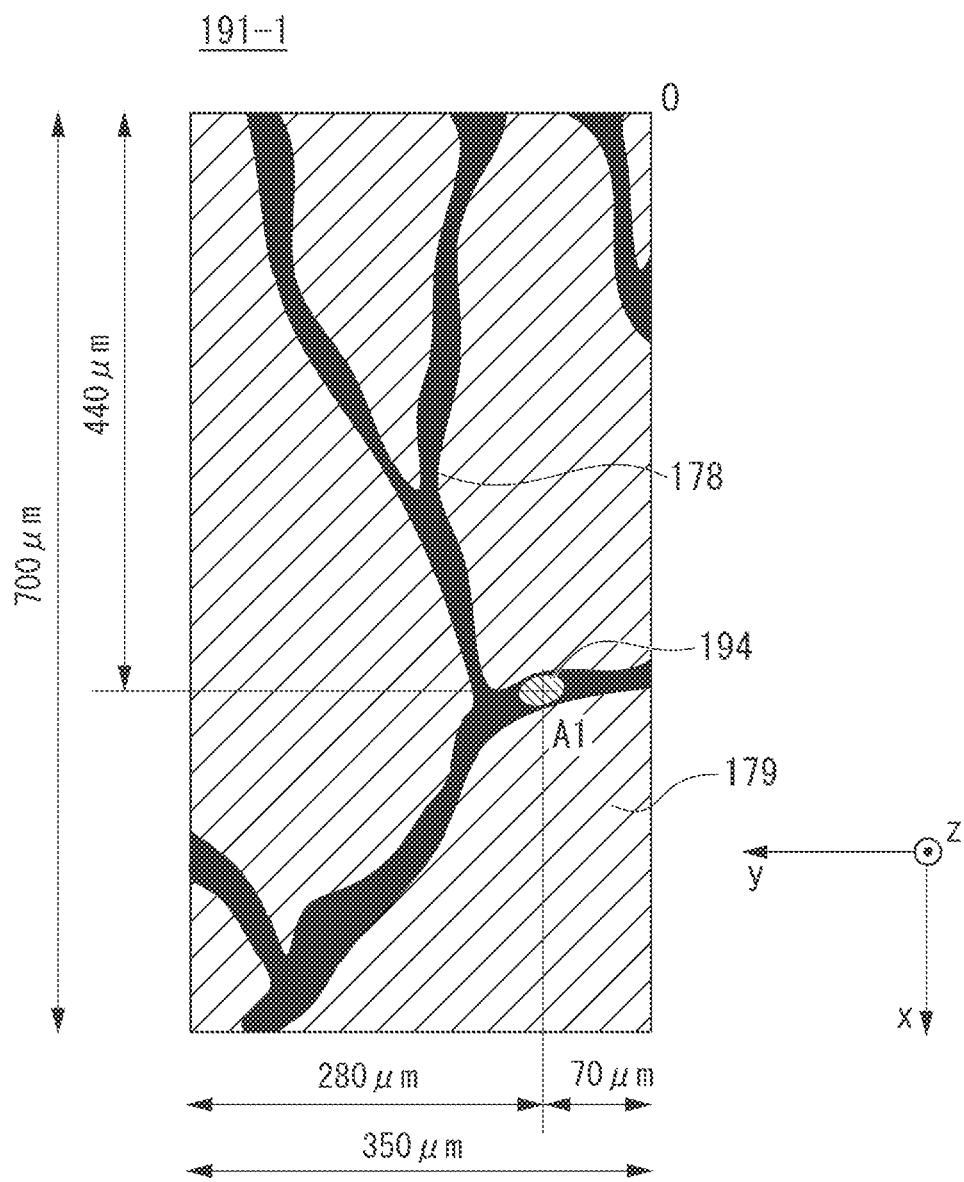
FIGS. 3A and 3B illustrate an example blood flow velocity calculation method that can be realized by the SLO apparatus according to the first exemplary embodiment of the present invention.
Figure 3B:
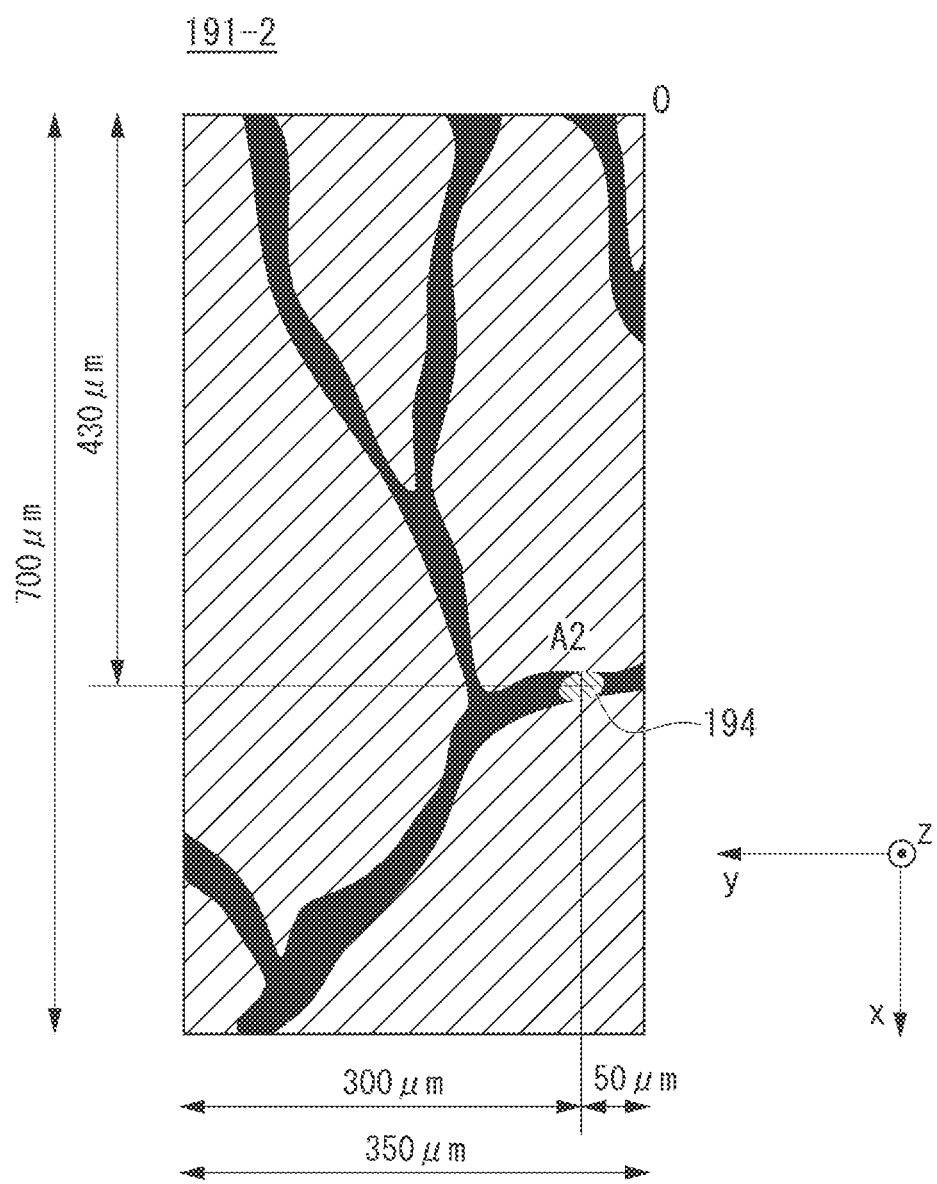

FIGS. 3A and 3B illustrate two temporally continuous planar images 191-1 and 191-2 that have been acquired according to the above-described method. These planar images 191-1 and 191-2 can be displayed in parallel to each other on the display device of the personal computer 125. The planar images illustrated in FIGS. 3A and 3B include the blood vessel 178, the photoreceptor cell group 179, and the blood cell 194. An example method for calculating moving velocity of the blood cell 194, i.e., the blood flow velocity, based on the above-described planar images 191-1 and 191-2 is described.

The blood flow velocity calculation method includes the following processes (1) to (5). A computer can be used to perform the following processes automatically.

In the process (1), the personal computer 125 performs image processing on each of the planar images 191-1 and 191-2 in such a way as to display a highlighted image of the blood cell 194. For example, the personal computer 125 regards the photoreceptor cell group 179 as a temporally fixed object and obtains the image of the blood cell 194 to be highlighted based on a difference between the planar images 191-1 and 191-2. Further, the personal computer 125 can correct a distortion that may be caused in an involuntary eye movement during fixation for each of the planar images 191-1 and 191-2.

In the process (2), the personal computer 125 acquires the position of the blood cell 194 in each of the planar images 191-1 and 191-2. In the present exemplary embodiment, if the origin O (0, 0) is the upper right corner of each image, the position (measurement unit: μm) of the blood cell 194 is A1 (70, 440) in the planar image 191-1 and A2 (50, 430) in the planar image 191-2. A computer can acquire the position of the blood cell 194 automatically. An operator can select the blood cell 194 with the mouse of the personal computer 125.

In the process (3), the personal computer 125 calculates a traveled distance L (measurement unit: μm) based on each position of the blood cell 194 acquired in the process (2). The traveled distance L can be expressed using the difference between two positions A1 and A2, i.e., L (20, 10).

In the process (4), the personal computer 125 calculates traveling time T considering the direction of the raster scanning. The traveling time T is the time required for the blood cell 194 to travel the distance L calculated in the process (3). The sub scanning direction of the measuring beam 106 is the positive Y direction in the planar image 191-1 and the negative Y direction in the planar image 191-2. Further, the size of the planar image 191 is 700 μm×350 μm (i.e., 400 pixels×200 pixels in the present exemplary embodiment). The frequency of the Y scanner is 38 Hz.

The time required for the Y scanner to scan the planar images 191-1 and 191-2 is ⅟₃₈ [s]. Accordingly, the traveling time T is 0.0218 s (=(1/(38×2))×(280/350+300/350)). In the present exemplary embodiment, the X scanner can operate at speeds sufficiently higher than those of the Y scanner. Therefore, the personal computer 125 can neglect the traveling time in the X direction.

In the process (5), the personal computer 125 calculates the blood flow velocity. In this case, moving velocity V (measurement unit: mm/s) of the blood cell 194 can be defined by V=L/T. Therefore, the personal computer 125 obtains the moving velocity V=(0.917, 0.459). The magnitude of the blood flow velocity is 1.03 mm/s.

A measuring range for Y-directional moving velocity Vy of the blood cell 194 is described below. The maximum Y-directional moving velocity Vy that can be measured based on the continuously acquired planar images 191-1 and 191-2 is described in detail below in a case A where a blood cell moving direction is similar to the sub scanning direction and in a case B where the blood cell moving direction is different from the sub scanning direction.

In the case A, the blood cell 194 moves from the right edge of the planar image 191-1 to the left edge of the planar image 191-2. The moving velocity Vy is 26.6 mm/s (=350/(1/(38×2))).

In the case B, the blood cell 194 moves from the left edge of the planar image 191-1 to the right edge of the planar image 191-2. The moving velocity Vy is −26.6 mm/s (=−350/(1/(38×2))). Accordingly, the absolute value of the moving velocity Vy is the same in both the positive and negative sub scanning directions.

The scanning operation is conventionally performed in either the positive Y direction or the negative Y direction. Therefore, the measuring range for the blood flow velocity is dependent on the scanning direction. However, in the present exemplary embodiment, the scanning speed in the positive Y direction is similar to the scanning speed in the negative Y direction. Therefore, the measuring range for the blood flow velocity is not dependent on the scanning direction. In the present exemplary embodiment, the terminology "similar" means not only "perfectly identical" but also "substantially the same."

The conventional scanning method includes first performing scanning from the point S to the point E (see FIG. 2D), and then performing scanning from the point E to the point S, and further performing scanning again from the point S to the point E. In this case, the time required to perform scanning from the point E to the point S is short compared to the time required to perform scanning from the point S to the point E. Therefore, the measuring range in the above-described case B where the blood cell moving direction is different from the sub scanning direction is wider than the measuring range in the above-described case A where the blood cell moving direction is similar to the sub scanning direction.

The above-described relationship is similarly recognized even in a case where the sub scanning direction is opposite as illustrated in FIG. 2F. More specifically, the measuring range according to the conventional scanning method is substantially dependent on the sub scanning direction. In other words, the measuring range according to the conventional scanning method is variable depending on the blood flow direction.

As described above, if the sub scanning direction of the measuring beam can be reversed when the apparatus acquires planar images continuously, the measuring range for the blood flow velocity to be calculated can be obtained irrespective of the sub scanning direction. In other words, the measuring range becomes constant and does not vary depending on the blood flow direction.

Further, if the measuring beam speed in the vertical scanning for the first image can be equalized with that for the second image, the measuring range for the blood flow velocity to be calculated does not vary depending on the sub scanning direction.

Further, if the scanning angle of the Galvano scanner that performs sub scanning can be changed to form a temporally triangular wave shape, the measuring beam speed in the vertical scanning remains the same and the measuring range for the blood flow velocity to be calculated does not vary depending on the sub scanning direction.

Further, if the method includes calculating a time difference between two blood cell images captured at blood cell positions along a moving path of a blood cell in a blood vessel and calculating the moving velocity of the blood cell based on the calculated time difference, the blood flow velocity can be calculated accurately.

Further, if the method includes performing image processing appropriately on each captured planar image to display a highlighted image of the blood cell, the blood flow velocity can be calculated accurately. Further, the blood flow velocity can be calculated with higher probability.

Further, if a blood cell can be manually selected from a planar image, the blood flow velocity can be calculated with higher probability, for example, even when the planar image has a lower S/N ratio.

Further, if a blood cell can be automatically selected from a planar image, the blood flow velocity can be calculated easily.

Further, if the method includes generating and displaying a spatiotemporal image based on continuously captured planar image, the moving blood cell or the blood flow velocity can be easily detected.

Further, if the apparatus includes the spatial light modulation unit configured to modulate at least one of the measuring beam and the returned beam, the aberration measurement unit configured to measure the aberration generated by the subject's eye, and the control unit configured to control the modulation amount by the spatial light modulation unit to correct the aberration based on the measurement result obtained by the aberration measurement unit, and if the spatial light modulation unit is configured to perform modulation at a position optically conjugate with the aberration measurement unit, a planar image having excellent horizontal resolution can be acquired and the blood flow velocity of a thin blood vessel can be calculated.

An optical image capturing apparatus according to a second exemplary embodiment is a composite apparatus that includes an SLO apparatus and an optical coherence tomography (OCT) apparatus. In particular, the composite apparatus according to the second exemplary embodiment includes an adaptive optics system and can capture a planar image (i.e., a SLO image) of a retina having excellent horizontal resolution as well as a tomographic image (i.e., an OCT image), and can calculate the blood flow velocity based on an acquired planar image.

The SLO apparatus according to the present exemplary embodiment includes a spatial optical modulator that can correct an optical aberration of a subject's eye to acquire a planar image. The OCT apparatus according to the present exemplary embodiment is a Fourier domain type that can acquire a tomographic image. The OCT apparatus according to the present exemplary embodiment can obtain an excellent planar image and a tomographic image that are not influenced by diopter or optical aberration of the subject's eye.

Although the Fourier domain OCT apparatus is described in detail below, the OCT apparatus according to the present exemplary embodiment is not limited to this type. For example, the time domain OCT apparatus is employable.

First, a schematic configuration of a composite apparatus 100 according to the present exemplary embodiment is described in detail below with reference to FIG. 4. The configuration illustrated in FIG. 4 includes constituent components that are similar to those of the SLO apparatus according to the first exemplary embodiment illustrated in FIG. 1. The detailed descriptions thereof are not repeated.

An optical coupler 131 can split light received from a light source 101 into a reference beam 105 and a measuring beam 106. The composite apparatus 100 can guide the measuring beam 106 to a subject's eye 107 (i.e., an observation target) via a single mode fiber 130-4, a spatial optical modulator 159, an XY scanner 119, an X scanner 121, and a plurality of spherical mirrors 160-1 to 160-9.

The measuring beam 106 reflects and scatters when it meets the subject's eye 107 and travels as an returned beam 108 toward a detector 138 or a line sensor 139. The detector 138 can convert the light intensity of the returned beam 108 into a voltage signal. The detector 138 can form a planar image of the subject's eye 107 based on the obtained voltage signal. Further, the detector 138 can calculate blood flow velocity based on the acquired planar image.

Further, the line sensor 139 can mix the reference beam 105 and the returned beam 108 and can form a tomographic image of the subject's eye 107. Further, the line sensor 139 can extract a three-dimensional flow path of a blood vessel based on a plurality of acquired tomographic images.

The spatial optical modulator 159 according to the present exemplary embodiment is used as a device having a capability of correcting a wavefront aberration. However, a mirror having a variable shape is usable if it can correct the wavefront aberration.

The light source 101 is similar to that used in the first exemplary embodiment, which is suitable to capture a tomographic image.

The reference beam 105 travels along the following optical path. The reference beam 105 split by the optical coupler 131 can reach a lens 135-1 via a single mode fiber 130-2. The reference beam 105, after passing through the lens 135-1, travels as a parallel beam having a beam diameter of 4 mm.

Then, after being reflected by the mirrors 157-1 to 157-4, the reference beam 105 can reach a mirror 114 (i.e., a reference mirror). The optical path length of the reference beam 105 is set to be substantially equal to the optical path length of the measuring beam 106. Therefore, the reference beam 105 and the measuring beam 106 can interfere with each other.

Then, after being reflected by the mirror 114, the reference beam 105 can return to the optical coupler 131. In the present exemplary embodiment, the reference beam 105 passes through a dispersion compensating glass 115, which can compensate a dispersion component for the reference beam 105 when the measuring beam 106 travels toward and returns from the subject's eye 107. In the present exemplary embodiment, the diameter of an eyeball is set to a representative value for Japanese (more specifically, L1=23 mm).

Further, a driver unit 181 can move an electric stage 117-1 in a direction indicated by an arrow to adjust the optical path length of the reference beam 105. To this end, the personal computer 125 controls an electric stage driver 183 provided in the driver unit 181 to drive the electric stage 117-1.

The measuring beam 106 travels along the following optical path. The measuring beam 106 split by the optical coupler 131 can reach a lens 135-4 via the single mode fiber 130-4. The measuring beam 106, after passing through the lens 135-4, travels as a parallel beam having a beam diameter of 4 mm.

Further, a polarizing controller 153-1 or 153-2 can adjust a polarizing state of the measuring beam 106. In the present exemplary embodiment, the polarizing controller 153-1 or 153-2 adjusts the polarizing state of the measuring beam 106 to be linearly polarized in a direction parallel to the drawing surface.

The measuring beam 106 passes through a beam splitter 158 and a movable beam splitter 161 (which may be referred to as a "branching unit") and reaches the spatial optical modulator 159 via the spherical mirrors 160-1 and 160-2.

In the present exemplary embodiment, the spatial optical modulator 159 is a modulator that utilizes the orientation characteristics of the liquid crystal to modulate the measuring beam 106. More specifically, the spatial optical modulator 159 is disposed in a predetermined direction where the spatial optical modulator 159 can modulate the phase of linear polarization parallel to the drawing surface (i.e., the P polarization) to coincide with the polarization orientation of the measuring beam 106.

Further, the measuring beam 106 passes through a polarizing plate 173 and reaches a mirror of the X scanner 121 via spherical mirrors 160-3 and 160-4. In the present exemplary embodiment, the polarizing plate 173 has a role to guide only the linear polarization parallel to the drawing surface, of the returned beam 108, to the spatial optical modulator 159.

Further, in the present exemplary embodiment, the X scanner 121 is an X scanner that performs scanning with the measuring beam 106 in a direction parallel to the drawing surface. For example, the X scanner 121 is a resonance scanner having a driving frequency of approximately 7.9 kHz.

Further, the measuring beam 106 reaches a mirror of the XY scanner 119 via the spherical mirrors 160-5 and 160-6. In the present exemplary embodiment, the XY scanner 119 illustrated in FIG. 4 has only one mirror. However, in an actual arrangement, two mirrors are disposed adjacently for an X scanner and a Y scanner.

Further, the center of the measuring beam 106 coincides with a rotational center of the mirror provided in the XY scanner 119. The driving frequency of the XY scanner 119 is variable in the range 0 to 500 Hz.

The spherical mirrors 160-7 to 160-9 can constitute an optical system that can perform scanning on a retina 127. The optical system has a role to scan the retina 127 with the measuring beam 106 around a fulcrum positioned in the vicinity of a cornea 126.

In the present exemplary embodiment, the measuring beam 106 has a beam diameter of 4 mm. However, the beam diameter of the measuring beam 106 may be large enough to acquire a high-resolution tomographic image.

Further, the driver unit 181 can move an electric stage 117-2 in a direction indicated by an arrow to adjust and control the position of the associated spherical mirror 160-8.

The personal computer 125 can control the electric stage driver 183 to drive the electric stage 117-2.

When the driver unit 181 moves the electric stage 117-2 to adjust the position of the spherical mirror 160-8, the measuring beam 106 can be focused on a predetermined layer of the retina 127 of the subject's eye 107, and can be visually recognized. The position of the spherical mirror 160-8 is initially adjusted to let the measuring beam 106 travel as a parallel beam and reach the cornea 126.

Further, for example, if the subject's eye 107 has refraction abnormality, it is useful to adjust the position of the spherical mirror 160-8. The measuring beam 106 reflects and scatters on the retina 127 when the measuring beam 106 meets the subject's eye 107 and travels as the returned beam 108 toward the optical coupler 131 again, and reaches the line sensor 139.

Further, after being reflected by the movable beam splitter 161, a part of the returned beam 108 reaches the detector 138 via a lens 135-5. In the present exemplary embodiment, a light-shielding plate 172 with a pinhole has a role to block unnecessary light (i.e., a light component that has not focused at the retina 127) of the returned beam 108.

Further, the light-shielding plate 172 is disposed at a position conjugate with the in-focus position of the lens 135-5. For example, the pinhole of the light-shielding plate 172 has a diameter of 50 μm. The detector 138 is, for example, a high-speed and sensitive optical sensor, such as Avalanche Photo Diode (APD).

Further, a part of the returned beam 108 split by the beam splitter 158 reaches the wavefront sensor 155. The wavefront sensor 155 is a Shack-Hartmann wavefront sensor.

In the present exemplary embodiment, the spherical mirrors 160-1 to 160-9 are disposed in such a way that the XY scanner 119, the X scanner 121, the cornea 126, the wavefront sensor 155, and the spatial optical modulator 159 are optically conjugate with each other. Therefore, the wavefront sensor 155 can measure the aberration of the subject's eye 107.

Further, the spatial optical modulator 159 can correct the aberration of the subject's eye 107. Further, when the personal computer 125 performs real-time control for the spatial optical modulator 159 based on the obtained aberration, the aberration generated by the subject's eye 107 can be corrected, and a tomographic image having excellent horizontal resolution can be acquired.

An example configuration of the measurement system is described below. The composite apparatus 100 can acquire both a tomographic image (i.e., an OCT image) and a planar image (i.e., an SLO image).

A tomographic image measurement system has the following configuration. The optical coupler 131 combines the returned beam 108 with the reference beam 105. Mixed light 142 reaches a transmission grating 141 via a single mode fiber 130-3 and a lens 135-2. After being dispersed for each wavelength by the transmission grating 141, the mixed light 142 finally reaches the line sensor 139 via a lens 135-3.

The line sensor 139 converts the intensity of the light 142 into a voltage signal for each position (i.e., wavelength). A frame grabber 140 converts the voltage signal into a digital value. The personal computer 125 forms a tomographic image of the subject's eye 107.

In the present exemplary embodiment, the line sensor 139 includes 1,024 pixels, and can detect the intensity of the mixed light 142 for each wavelength (each of 1,024 subsections).

A planar image measurement system has the following configuration. The movable beam splitter 161 reflects a part of the returned beam 108. The light-shielding plate 172 blocks unnecessary light components of the reflected light.

Then, the light reaches the detector 138. The detector 138 converts the intensity of the light into an electric signal.

The personal computer 125 performs data processing on the obtained electric signal in synchronization with scan signals of the X scanner 121 and the XY scanner 119, and forms a planar image.

A part of the returned beam 108 split by the beam splitter 158 reaches the wavefront sensor 155. The wavefront sensor 155 measures an aberration of the returned beam 108. The personal computer 125 receives an image signal obtained by the wavefront sensor 155 and calculates an aberration value. The obtained aberration (i.e., the aberration of the subject's eye 107) can be expressed using Zernike polynomials.

The Zernike polynomial expression includes a tilt term, a defocus term, an astigmatism term, a coma term, and a trifoil term.

An example tomographic image (i.e., OCT image) acquisition method that can be realized by the composite apparatus 100 is described below with reference to FIGS. 5A to 5C.

The composite apparatus 100 controls the XY scanner 119 and causes the X scanner 121 to serve as a stationary mirror, while the line sensor 139 acquires interference fringes to acquire a tomographic image of the retina 127. Further, the composite apparatus 100 controls the movable beam splitter 161 to prevent the returned beam 108 from reaching the detector 138.

Figure 4:
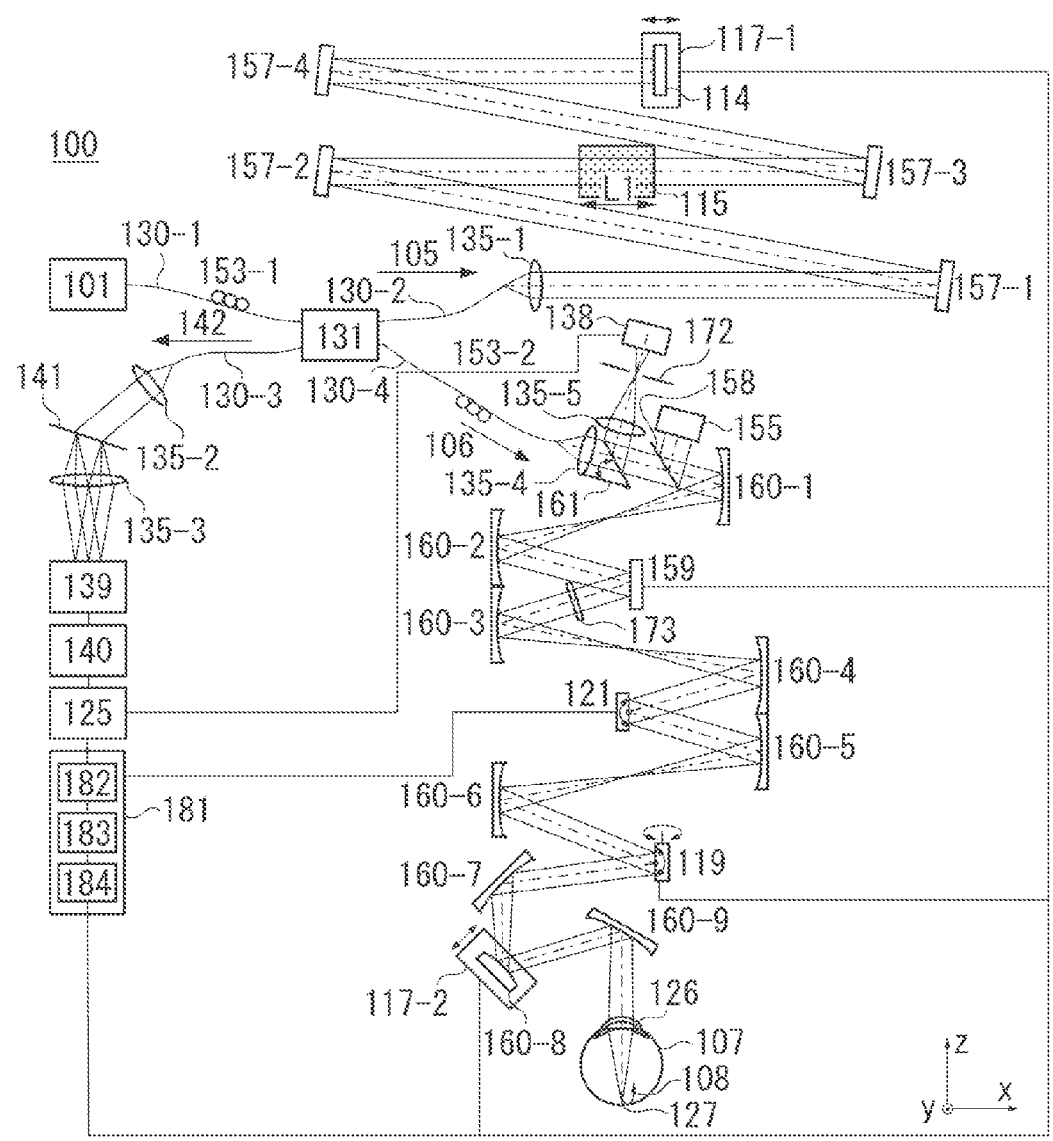
FIG. 4 illustrates an overall configuration of a composite apparatus according to a second exemplary embodiment of the present invention.

Further, the personal computer 125 controls an optical scanner driver 182 provided in the driver unit 181 to drive the X scanner 121 and the XY scanner 119 (see FIG. 4). The composite apparatus 100 can acquire a tomographic image (i.e., an image on a plane parallel to the optical axis) of the retina 127 in the following manner. FIG. 5A schematically illustrates the subject's eye 107, which can be observed by the composite apparatus 100.

Figure 5A:
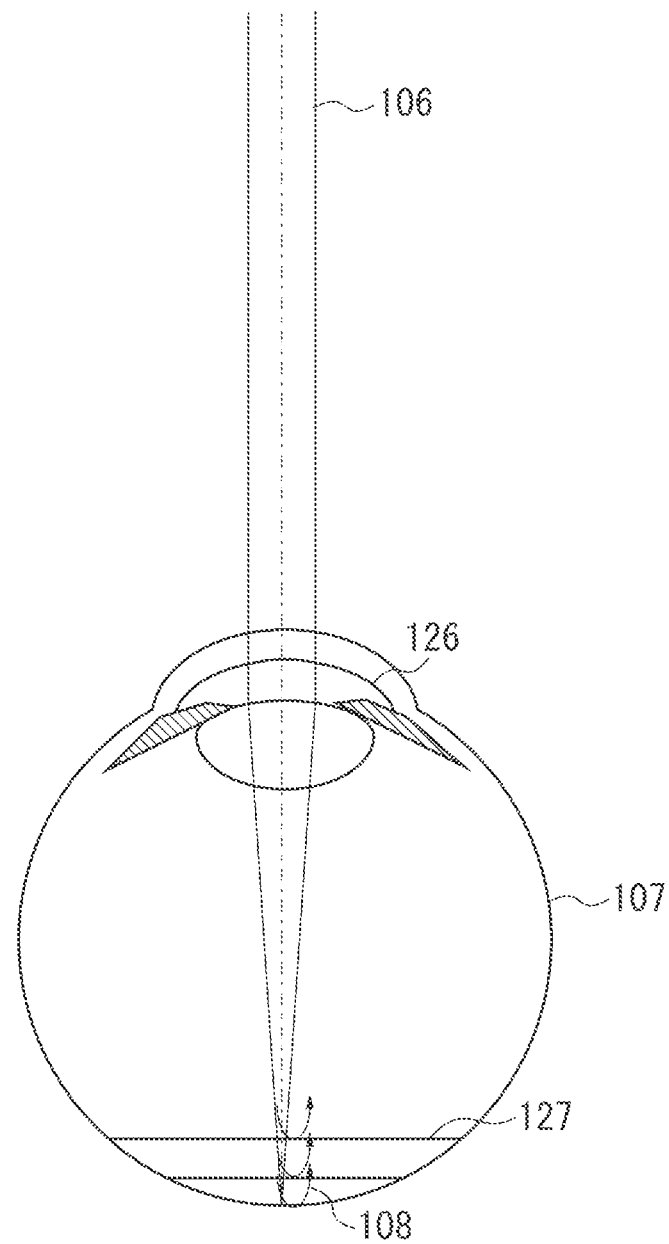

As illustrated in FIG. 5A, the measuring beam 106 reaches the retina 127 after passing through the cornea 126 and reflects and scatters at various positions, and then travels as the returned beam 108 and reaches the line sensor 139 with time delay that depends on each position.

In the present exemplary embodiment, the light source 101 has a wide bandwidth and a short coherence length. Therefore, if the length of the reference optical path is substantially equal to the length of the measurement optical path, the line sensor 139 can detect interference fringes.

As described above, the line sensor 139 can acquire interference fringes in a spectral area on the wavelength axis.

Next, the composite apparatus 100 converts the interference fringes (i.e., information obtained from the wavelength axis) into interference fringes on an optical frequency axis considering characteristics of the line sensor 139 and the transmission grating 141. Further, the composite apparatus 100 obtains information in the depth direction by applying inverse Fourier transformation to the converted interference fringes on the optical frequency axis.

Figure 5B:
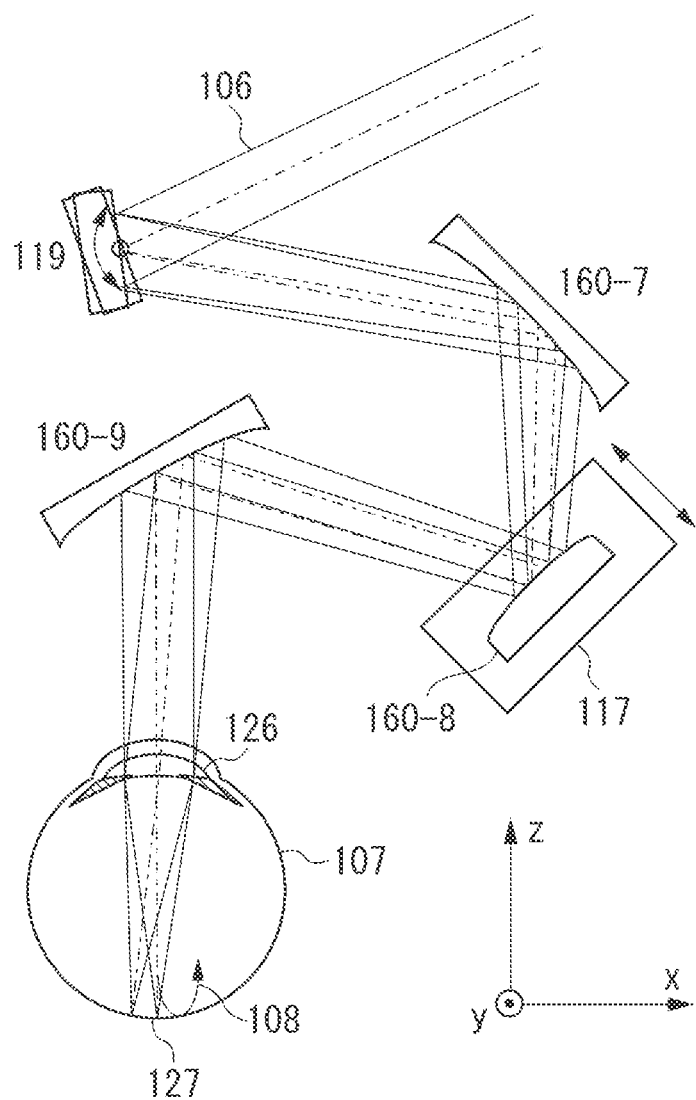

Further, as illustrated in FIG. 5B, the composite apparatus 100 can obtain interference fringes for each position along the X axis while driving the XY scanner 119. More specifically, the composite apparatus 100 can obtain the information in the depth direction at each position along the X axis.

As a result, the composite apparatus 100 can obtain a two-dimensional intensity distribution of the returned beam 108 on the XZ plane. More specifically, the composite apparatus 100 can form a tomographic image 132 (see FIG. 5C).

In general, the tomographic image 132 is composed of intensity components of the returned beam 108 arrayed as described above. For example, the composite apparatus 100 can display the tomographic image 132 by applying the gray scale to the intensity components. The length of the tomographic image 132 in the X directional is 700 μm, which is similar to that of the SLO image described below.

The tomographic image 132 illustrated in FIG. 5C includes highlighted boundary lines that represent a pigmented layer of retina 146 and an optic layer 147. The tomographic image 132 further includes a blood vessel 178. Further, the composite apparatus 100 can depict a three-dimensional flow path of the blood vessel by acquiring a plurality of tomographic images at numerous positions along the Y axis.

Next, an example planar image (i.e., SLO image) acquisition method that can be realized by the composite apparatus 100 is described below.

The composite apparatus 100 controls the XY scanner 119 in the Y axis and also controls the X scanner 121, while preventing the XY scanner 119 from moving in the X axis. The composite apparatus 100 acquires a planar image of the retina 127 based on intensity values of the returned beam 108 detected by the detector 138.

The personal computer 125 can control the optical scanner driver 182 of the driver unit 181 to drive the X scanner 121 and the XY scanner 119 (see FIG. 4). Further, the composite apparatus 100 can control the spatial optical modulator 159 based on an aberration of the subject's eye 107 measured by the wavefront sensor 155. The composite apparatus 100 can acquire planar images while correcting aberration generated by the subject's eye 107. Further, the composite apparatus 100 can acquire planar images by performing real-time control for the spatial optical modulator 159.

Since the planar image acquisition method according to the present exemplary embodiment is similar to the method described in the first exemplary embodiment, its description is not repeated.

Since the method for calculating the blood flow velocity based on acquired planar images according to the present exemplary embodiment is similar to the method described in the first exemplary embodiment, its description is not repeated.

The above-described blood vessel depicted on each acquired planar image can be regarded as an image of the three-dimensionally flowing blood vessel projected on the XY plane. Therefore, the measured blood flow velocity has a value on the XY plane. As described above, the apparatus can detect the three-dimensional stream of the blood vessel using a plurality of tomographic images, and can calculate a velocity value in the XYZ space based on the measured blood flow velocity on the XY plane.

As described above, the optical image capturing apparatus according to the present invention includes the splitting unit configured to split light received from the light source into the measuring beam and the reference beam, the unit configured to cause the returned measuring beam traveling from the subject's eye to interfere with the reference beam traveling via the reference optical path, and the detection unit configured to detect the intensity of the interference signal representing the interference. The optical image capturing apparatus according to the present invention has a function of capturing a tomographic image of the subject's eye. Therefore, the optical image capturing apparatus according to the present invention can use the entire optical system not only for tomographic image capturing but also for planar image capturing. Thus, the optical image capturing apparatus according to the present invention can capture both the planar image and the tomographic image with a simple configuration and can detect a three-dimensional stream of a blood vessel. Further, the optical image capturing apparatus according to the present invention can calculate the blood flow velocity in the XYZ space (i.e., the three-dimensional space).

Further, the present invention can be realized by executing the following processing. Specifically, the processing includes supplying a software program that can realize the functions of the above-described exemplary embodiments to a system or an apparatus via a network or an appropriate storage medium and causing a computer (or a central processing unit (CPU) or a micro-processing unit (MPU)) of the system or the apparatus to read and execute the program.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2010-269740 filed Dec. 2, 2010, which is hereby incorporated by reference herein in its entirety.

What is claimed is:

1. An ophthalmologic apparatus comprising:
   an irradiation unit configured to irradiate a subject's eye with a measuring beam emitted by a scanning unit that performs scanning;
   a first acquisition unit configured to acquire a first image of the subject's eye based on the returned measuring beam from the subject's eye when the scanning unit performs scanning in a first sub scanning direction;
   a second acquisition unit configured to acquire a second image of the subject's eye based on the returned measuring beam that travels from the subject's eye, continuously from acquisition of the first image, while the scanning unit performs scanning in a second sub scanning direction, which is opposite to the first sub scanning direction; and
   a calculation unit configured to calculate blood flow velocity of the subject's eye based on a blood cell position in the first image and a blood cell position in the second image as well as based on the sub scanning direction of the scanning unit.

2. The ophthalmologic apparatus according to claim 1, wherein a scanning speed in the first sub scanning direction is similar to a scanning speed in the second sub scanning direction.

3. The ophthalmologic apparatus according to claim 1, wherein the scanning unit is driven in such a way that a scanning angle changes temporally in a triangular wave shape.

4. The ophthalmologic apparatus according to claim 1, wherein the calculation unit is configured to calculate the blood flow velocity of the subject's eye based on a blood cell position in the first image, a blood cell position in the second image, the sub scanning direction of the scanning unit, and a scanning speed of the scanning unit.

5. The ophthalmologic apparatus according to claim 1, further comprising:
   a display unit configured to display the first image and the second image.

6. The ophthalmologic apparatus according to claim 5, further comprising:
   an image processing unit configured to perform image processing on the first image and the second image in such a way as to highlight the blood cell included in each of the first image and the second image when the image is displayed on the display unit.

7. The ophthalmologic apparatus according to claim 6, further comprising:
   a selection unit configured to select the blood cell included in the first image and the second image displayed on the display unit,
   wherein the calculation unit is configured to calculate the blood flow velocity of the subject's eye based on the blood cells included in the first image and the second image selected by the selection unit.

8. The ophthalmologic apparatus according to claim 1, further comprising:
   an image generation unit configured to generate a spatiotemporal image based on the first image and the second image.

9. The ophthalmologic apparatus according to claim 1, further comprising:
   an aberration measurement unit configured to measure an aberration generated by the subject's eye;
   a spatial light modulation unit, which is positioned to be optically conjugate with the aberration measurement unit, configured to modulate at least one of the measuring beam and the returned beam; and
   a control unit configured to control a modulation amount by the spatial light modulation unit to correct the aberration based on a measurement result obtained by the aberration measurement unit.

10. The ophthalmologic apparatus according to claim 1, further comprising:
    a splitting unit configured to split light received from a light source into the measuring beam and a reference beam;
    an interference unit configured to cause the returned measuring beam traveling from the subject's eye to interfere with the reference beam traveling via a reference optical path;
    a detection unit configured to detect the intensity of an interference signal caused by the interference; and
    a tomographic image acquisition unit configured to acquire a tomographic image of the subject's eye based on the intensity detected by the detection unit.

11. The ophthalmologic apparatus according to claim 10, further comprising:
    a conversion unit configured to detect the returned measuring beam from the subject's eye and convert the detected beam into an electric signal; and
    a light guiding unit positioned on an optical path connecting the light source and the subject's eye and configured to guide the returned beam toward the conversion unit,
    wherein the first acquisition unit and the second acquisition unit are configured to acquire the first image of the subject's eye and the second image of the subject's eye based on the intensity of the electric signal obtained by the conversion unit.

12. The ophthalmologic apparatus according to claim 10, wherein the calculation unit is configured to calculate blood flow velocity in a three-dimensional space, with reference to the blood flow velocity, based on a three-dimensional stream of a blood vessel of the subject's eye acquired using the tomographic image.

13. A blood flow velocity calculation method, comprising:
    irradiating a subject's eye with a measuring beam emitted by a scanning unit that performs scanning;
    acquiring a first image of the subject's eye based on the returned measuring beam from the subject's eye when the scanning unit performs scanning in a first sub scanning direction;
    acquiring a second image of the subject's eye based on the returned measuring beam that travels from the subject's eye, continuously from acquisition of the first image, while the scanning unit performs scanning in a second sub scanning direction, which is opposite to the first sub scanning direction; and
    calculating blood flow velocity of the subject's eye based on a blood cell position in the first image and a blood cell position in the second image as well as based on the sub scanning direction of the scanning unit.

14. The ophthalmologic apparatus according to claim 1, wherein the first sub scanning direction and the second sub scanning direction are perpendicular to a main scanning direction which is a horizontal direction of the subject's eye.

* * * * *